United States Patent [19]

Tomari et al.

[11] Patent Number: 4,946,844
[45] Date of Patent: Aug. 7, 1990

[54] OPTICALLY ACTIVE BENZOQUINOLIZINE COMPOUNDS, PROCESS FOR PREPARING SAME, AND ANTIBACTERIAL PREPARATION CONTAINING SAME AS ACTIVE INGREDIENT

[75] Inventors: Masazumi Tomari, Kawasaki; Yasuhiro Nagamatsu, Hasuda; Senji Suzuki, Tokyo, all of Japan

[73] Assignee: Tokyo Tanabe Co., Ltd., Tokyo, Japan

[21] Appl. No.: 286,467

[22] Filed: Dec. 19, 1988

[30] Foreign Application Priority Data

Dec. 26, 1987 [JP] Japan .................................. 62-328370
Oct. 21, 1988 [JP] Japan .................................. 63-264127

[51] Int. Cl.$^5$ ................. A61K 31/495; A61K 31/435; C07D 455/04
[52] U.S. Cl. ..................... 514/254; 544/361; 546/95
[58] Field of Search ............... 544/361; 546/95; 514/254

[56] References Cited

U.S. PATENT DOCUMENTS

| | | | |
|---|---|---|---|
| 4,117,229 | 9/1978 | Baker et al. | 548/301 |
| 4,195,176 | 3/1980 | Baker et al. | 536/24 |
| 4,683,341 | 7/1987 | Ishii et al. | 568/366 |
| 4,720,495 | 1/1988 | Takagi et al. | 544/361 |
| 4,818,394 | 4/1989 | Okamoto et al. | 536/64 |

FOREIGN PATENT DOCUMENTS 203795 12/1986 European Pat. Off. .

*Primary Examiner*—Cecilia Shen
*Attorney, Agent, or Firm*—McGlew & Tuttle

[57] ABSTRACT

An optically active (+)-isomer of a benzoquinolizine compound of the formula [I], is provided:

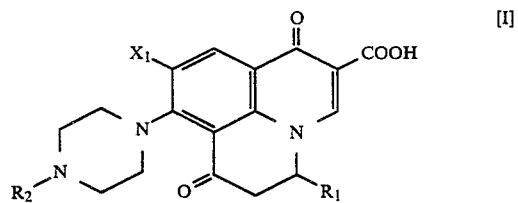

where $X_1$ represents a halogen atom, and $R_1$ and $R_2$ represent lower alkyl groups, a physiologically acceptable salt thereof, or a hydrate of either of the foregoing compounds. The compounds [I]-(+) exhibit an excellent antibacterial activity. Also, the compounds exhibit high solubility in water. Therefore, the compounds of the present invention are usable for the treatment of infectious diseases and usable in aqueous liquid preparations such as injections.

21 Claims, No Drawings

OPTICALLY ACTIVE BENZOQUINOLIZINE COMPOUNDS, PROCESS FOR PREPARING SAME, AND ANTIBACTERIAL PREPARATION CONTAINING SAME AS ACTIVE INGREDIENT

BACKGROUND OF THE INVENTION

Field of the Invention

This invention relates to (A) optically active benzoquinolizine compounds, (B) processes for preparing such compounds, and (C) antibacterial preparations containing such a compound as the active ingredient. They are more specifically described hereinbelow.

(A) Optically Active Benzoquinolizine Compounds (1) Optically active (+)-isomers (hereinafter referred to as compounds [I]-(+)) of benzoquinolizine compounds (hereinafter referred to as compounds [I]) of the formula

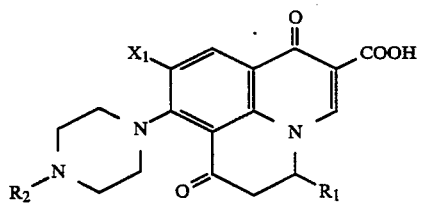

where $X_1$ represents a halogen atom, and $R_1$ and $R_2$ represent lower alkyl groups, physiologically acceptable salts thereof, or hydrates of the foregoing compounds. Compounds [I]-(+) have antibacterial activity and are useful as drugs.

(2) Optically active (+)-isomers (hereinafter referred to as compounds [II]-(+)) of benzoquinolizine compounds (hereinafter referred to as compounds [II]) of the formula

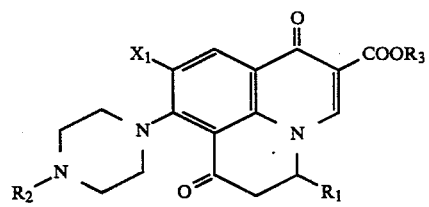

where $X_1$ represents a halogen atom, and $R_1$, $R_2$ and $R_3$ represent lower alkyl groups. Compounds [II]-(+) are useful as intermediates for the synthesis of compounds [I]-(+).

(3) Optically active (−)-isomers (hereinafter referred to as compounds [III]-(−)) of benzoquinolizine compounds (hereinafter referred to as compounds [III]) of the formula

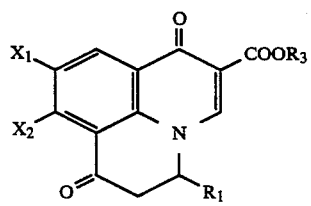

where $X_1$ and $X_2$ represent halogen atoms, and $R_1$ and $R_3$ represent lower alkyl groups. Compounds [III]-(−) are useful as intermediates for the synthesis of compounds [II]-(+).

(4) Optically active (−)-isomers (hereinafter referred to as compounds [IV]-(−)) of quinoline compounds (hereinafter referred to as compounds [IV]) of the formula

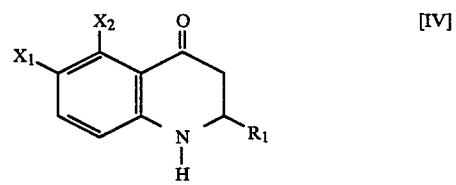

where $X_1$ and $X_2$ represent halogen atoms, and $R_1$ represents a lower alkyl group. Compounds [IV]-(−) are useful as intermediates for the synthesis of compounds [III]-(−).

(5) Optically active (+)-isomers (hereinafter referred to as compounds [V]-(+)) of anilinobutyric acid compounds (hereinafter referred to as compounds [V]) of the formula

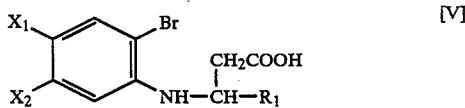

where $X_1$ and $X_2$ independently represent fluorine or chlorine atoms, and $R_1$ represents a lower alkyl group. Compounds [V]-(+) are useful as intermediates for the synthesis of compounds [IV]-(−).

(B) Processes for Preparing Optically Active Benzoquinolizine Compounds (1) Processes for preparing compounds [I]-(+)

(a) A process for preparing a compound [I]-(+), a physiologically acceptable salt thereof, or a hydrate of either of the foregoing compounds which comprises optically resolving the corresponding compound [I], a salt thereof, or a hydrate of a either of the foregoing compounds, in a solvent containing a metallic ion and an amino acid, with the aid of a resolving agent containing octadecylsilylated silica gel as a component.

(b) A process for preparing a compound [I]-(+), a physiologically acceptable salt thereof, or a hydrate of either of the foregoing compounds which comprises hydrolyzing the corresponding compound [II]-(+).

(c) A process for preparing a compound [I]-(+), a physiologically acceptable salt thereof, or a hydrate of either of the foregoing compounds which comprises effecting nucleophilic substitution reaction between an optically active (−)-isomer (hereinafter referred to as a compound [VI]-(−)) of a benzoquinolizine compound (hereinafter referred to as a compound [VI]) of the formula

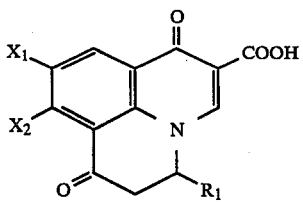

[VI]

where $X_1$ and $X_2$ represent halogen atoms, and $R_1$ represents a lower alkyl group, and a piperazine compound (hereinafter referred to as a compound [VII]) of the formula

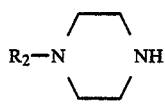

[VII]

where $R_2$ represents a lower alkyl group.

(2) Process for preparing compounds [II]-(+)

A process for preparing a compound [II]-(+) which comprises optically resolving the corresponding compound [II] with the aid of a resolving agent containing a polysaccharide compound as an active component.

(3) Process for preparing compounds [III]-(−)

A process for preparing a compound [III]-(−) which comprises optically resolving the corresponding compound [III] with the aid of a resolving agent containing a polysaccharide compound as an active component.

(4) Process for preparing compounds [IV]-(−)

A process for preparing a compound [IV]-(−) which comprises optically resolving the corresponding compound [IV] with the aid of a resolving agent containing a polysaccharide compound as an active component.

(5) Process for preparing compounds [V]-(+)

A process for preparing a compound [V]-(+) which comprises optically resolving the corresponding compound [V] with the aid of a resolving agent comprising an optically active amine.

(C) Antibacterial Preparations Containing an Optically Active Benzoquinolizine Compound as the Active Ingredient Antibacterial preparations containing, as the active ingredient, a compound [I]-(+), a physiologically active salt thereof, or a hydrate of either of the foregoing compounds.

DESCRIPTION OF THE PRIOR ART

Compounds [I] are described in Japanese Patent Laid-Open No. 53987/'87. It is known that they have good absorbability from the digestive tract into the blood and exhibit long-lasting antibacterial activity.

SUMMARY OF THE INVENTION

As a result of search for a compound having more potent antibacterial activity, the present inventors have found that the antibacterial activity of a compound [I]-(+) is about twice as potent as that of the corresponding compound [I] and about 8 to 128 times as potent as that of the optically activre (−)-isomer (hereinafter referred to as the compound [I]-(−)) of the compound [I], and that the compound [I]-(+) has markedly higher solubility in water than the compound [I]. The present invention has been completed on the basis of these findings.

(1) Compounds [I] can be prepared in the following manner.

A compound [IV] is reacted with a malonic ester compound of the formula

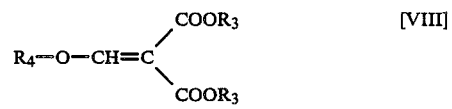

[VIII]

where $R_3$ represents a lower alkyl group and $R_4$ represents a methyl or ethyl group, to form a compound (hereinafter referred to as the compound [IX]) of the formula

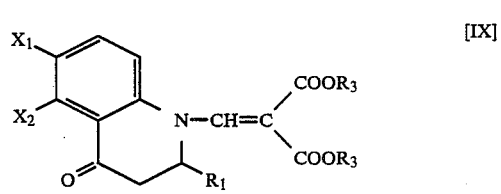

[IX]

where $X_1$ and $X_2$ represent halogen atoms, and $R_1$ and $R_3$ represent lower alkyl groups. This compound [IX] is converted into a compound [III] by cyclocondensation. Then, a compound [II] is formed by effecting nucleophilic substitution reaction between the compound [III] and a compound [VII]. Finally, the compound [II] is hydrolyzed to obtain a compound [I].

(2) The present processes for preparing compounds [I]-(+) are more specifically described below.

A compound [IV] is reacted with N-tosyl-L-prolyl chloride (hereinafter referred to as the compound [X]) of the formula

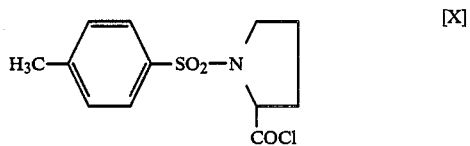

[X]

to form a mixture of diastereomers of a quinoline compound (hereinafter referred to as the compound [XI]) of the formula

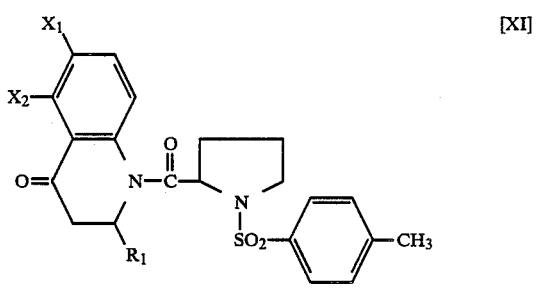

[XI]

where $X_1$ and $X_2$ represent halogen atoms and $R_1$ represents a lower alkyl group. This mixture is resolved by column chromatography or fractional crystallization to obtain the optically active (+)-isomer (hereinafter referred to as the compound [XI]-(+)) of the compound [XI]. At the same time, the optically active (−)-isomer (hereinafter referred to as the compound [XI]-(−)) of the compound [XI] is also obtained. The compound [XI]-(+) is hydrolyzed with an alkali to obtain a compound [IV]-(−). Similarly, a compound [IV]-(+) is obtained from the compound [XI]-(−).

The compound [IV]-(−) is reacted with a compound [VIII], preferably diethyl ethoxymethylenemalonate, and then reacted with heated polyphosphoric acid to form a compound [III]-(−). Similarly, a compound [III]-(+) is formed from the compound [IV]-(+). Then, the compound [III]-(−) is reacted with a compound [VII] to form a compound [II]-(+). Similarly, a compound [II]-(−) is formed from the compound [III]-(+). Finally, the desired compound [I]-(+) is obtained by hydrolyzing the compound [II]-(+) with an alkali and then adjusting the resulting solution to pH 4–5 with acetic acid.

If the solution resulting from the above-described alkali hydrolysis is adjusted to pH 1 by using hydrochloric acid in place of acetic acid, the hydrochloride of the compound [I]-(+) is obtained. The alkali hydrolysis may be replaced by acid hydrolysis. Similarly, a compound [I]-(−) is obtained from the compound [II]-(−).

Alternatively, a compound [I]-(+) can also be prepared by hydrolyzing a compound [III]-(−), which is an intermediate for the synthesis of the compound [I]-(+), to form an optically active (−)-isomer (hereinafter referred to as the compound [VI]-(−) of a compound [VI], and then effecting nucleophilic substitution reaction between the compound [VI]-(−) and a compound [VII].

(3) The present process for preparing a compound [I]-(+), a physiologically acceptable salt thereof, or a hydrate of either of the foregoing compounds by optical resolution is more specifically described below.

A compound [I], a salt thereof, or a hydrate of either of the foregoing compounds can be optically resolved in a solvent containing a metallic ion and an amino acid, with the aid of a resolving agent containing octadecylsilylated silica gel as a component.

When a compound [I] is resolved by reversed phase chromatography using a mobile phase containing copper and an amino acid, there are obtained a compound [I]-(+)-amino acid-copper complex and a compound [I]-(−)-amino acid-copper complex. The mobile phase contains 11 to 20%, preferably 15%, of methanol, contains the copper and the amino acid at concentrations of 1 to 4 mM, preferably 3 mM, and has a pH of 4.8 to 5.8, preferably 5.0 to 5.2. The copper may comprise a copper salt such as copper sulfate, and the amino acid may comprise L-valine, L-leucine, L-isoleucine, L-phenylalanine, D-phenylalanine or the like. The compound [I]-(+) and the [I]-(−) can be obtained by treating the aforesaid complexes with an ion exchange resin.

(4) The present process for preparing a compound [II]-(+) by optical resolution is more specifically described below.

A compound [II] is optically resolved by high-performance liquid chromatography using a resolving agent containing a polysaccharide compound as an active component. Useful resolving agents include, for example, CHIRALCEL OD, CHIRALCEL OG and CHIRALCEL OC (APS), all of which are products of Daicel Chemical Industries, Ltd. As the solvent for high-performance liquid chromatography, there may used n-hexane-isopropanol (9:1), methanol or ethanol.

(5) The present process for preparing a compound [III]-(−) or a compound [IV]-(−) by optical resolution is more specifically described below.

Similarly to the above-described process for preparing a compound [II]-(+), a salt thereof, or a hydrate of either of the foregoing compounds, a compound [III] or a compound [IV] is optically resolved by high-performance liquid chromatography using a resolving agent containing a polysaccharide compound as an active component.

(6) The present process for preparing a compound [V]-(+) by optical resolution is more specifically described below.

A compound [V] and an optically active amine are dissolved in a solvent by the applicaiton of heat. Fractional crystallization from this solution is carried out to obtain the amine salt of the compound [V]-(+), from which the amine is then eliminated. Optically active amines useful for this purpose include, for example, L-(−)-1-phenylethylamine and cinchonidine.

The compound [V]-(+) thus obtained is subjected to cyclocondensation in a mixture of triethyl phosphate and phosphorus pentoxide. The resulting product is debrominated by selective hydrogenation to obtain a compound [IV]-(−).

EFFECTS OF THE INVENTION

In Vitro Antibacterial Activity

The in vitro antimicrobial activity of a typical compound in accordance with the present invention (hereinafter referred to as the present compound) was evaluated in terms of minimum inhibitory concentrations for various Gram-positive and Gram-negative bacteria. The Gram-positive bacteria used as test microorganisms included *Bacillus subtilis, Staphylococcus aureus, Staphylococcus epidermidis* and *Streptococcus pyogenes,* and the Gram-negative bacteria used as test microorganisms included *Escherichia coli, Enterobacter cloacae, Klebsiella pneumoniae, Proteus vulgaris, Pseudomonas aeruginosa, Serratia marcescens, Salmonella enteritidis* and *Morganella morganii.* The minimum inhibitory concentrations (for the test microorganisms cultured at 37° C. for 20 hours) were determined according to the standard method prescribed by the Japanese Chemotherapeutic Society (Journal of the Japanese Chemotherapeutic Society, Vol. 29, No. 1, p. 76, 1981). As the present compound, there was used (+)-9-fluoro-5-methyl-8-(4-methyl-1-piperazinyl)-6,7-dihydro-1,7-dioxo1H,5H-benzo[ij]quinolizine-2-carboxylic acid hydrochloride monohydrate which had been prepared in Example 1 described later. For purposes of comparison, control compounds were evaluated in the same manner as described above. These control compounds comprised the optically active (−)-isomer of the aforesaid compound (which had been prepared in Reference Example described later) and the racemate thereof. The results thus obtained are shown in the following table.

TABLE

| Test microorganism | Minimum inhibitory concentration (μg/ml) | | |
|---|---|---|---|
| | Present compound | (−)-isomer | Racemate |
| *Bacillus subtilis* ATCC 6633 | 0.05 | 1.56 | 0.10 |
| *Staphylococcus aureus* FDA 209P JC-1 | 0.20 | 25 | 0.39 |
| *Staphylococcus epidermidis* IAM 1296 | 0.39 | 50 | 1.56 |
| *Streptococcus pyogenes* ATCC 19615 | 0.78 | >100 | 6.25 |
| *Escherichia coli* | 0.10 | 3.13 | 0.20 |

TABLE-continued

| Test microorganism | Minimum inhibitory concentration (μg/ml) | | |
|---|---|---|---|
| | Present compound | (−)-isomer | Racemate |
| NIHJ JC-2 | | | |
| Enterobacter cloacae 963 | 0.10 | 3.13 | 0.20 |
| Klebsiella pneumoniae PCI 602 | ≦0.025 | 0.78 | 0.10 |
| Proteus vulgaris ATCC 13315 | 0.10 | 0.78 | 0.20 |
| Pseudomonas aeruginosa PAO 1 | 0.78 | 12.5 | 1.56 |
| Serratia marcescens IAM 1184 | 0.39 | 3.13 | 1.56 |
| Salmonella enteritidis G 14 | 0.20 | 1.56 | 0.78 |
| Morganella morganii IFO 3848 | ≦0.025 | 0.78 | 0.10 |

It is evident from the above table that the antibacterial activity of the present compound is about twice as potent as that of the racemate and about 8 to 128 times as potent as that of the (−)-isomer.

Solubility

The solubilities of the present compound (which had been prepared in Example 1) and its racemate in water were determined. The solubility of the present compound was about 18 g/100 ml and that of the racemate was about 0.7 g/100 ml.

It can be seen from the above results that the solubility of the present compound is about 25 times as high as that of the racemate. Thus, the present invention is found to be more readily usable in aqueous liquid preparations such as injections. cl EXAMPLES The preparation of the present compounds is further illustrated by the following examples.

EXAMPLE 1

(Step a)

36.7g of (+)-5-chloro-6-fluoro-2-methyl-4-oxo1,2,3,4-tetrahydroquinoline was dissolved in 34.3 g of pyridine and 400 ml of dichloromethane. Then, a solution of N-tosyl-L-prolyl chloride (prepared from 92.4 g of N-tosyl-L-proline and 74.5 ml of thionyl chloride) in 70 ml of dichloromethane was added thereto at room temperature over a period of 20 minutes. After completion of the addition, the resulting mixture was stirred for 15 minutes and then heated under reflux for 20 minutes. This reaction mixture was allowed to cool, washed successively with dilute hydrochloric acid, an aqueous solution of sodium hydrogen carbonate and water, and then dried. Thereafter, the solvent was evaporated under reduced pressure to obtain a residue comprising a mixture diastereomers of 5-chloro-6-fluoro-2-methyl-4-oxo-1-(N-tosyl-L prolyl)-1,2,3,4-tetrahydroquinoline. This residue was subjected to silica gel column chromatography using chloroform-ethyl acetate (10:1) as the eluent, and then subjected to thin-layer chromatography [using chloroform-ethyl acetate (10:1) as the developing solvent]. Fractions having an Rf value of 0.47 were collected and concentrated under reduced pressure to obtain 36.8 g of (+)-5-chloro-6-fluoro-2-methyl-4-oxo-1-(N-tosyl-L-prolyl)-1,2,3,4-tetrahydroquinoline.

Melting point: 135.4°–136.4° C.

$[\alpha]_D^{20}$: +279.8° C. (C=1.006, CHCl$_3$).

IR (KBr), cm$^{-1}$: 1695, 1600, 1465, 1335.

NMR (CDCl$_3$), δppm: 1.25 (3H, d), 1.4–2.2 (4H, m), 2.42 (3H, s), 2.62 (1H, d), 3.03 (1H, dd), 3.3–3.5 (2H, m), 4.9-5.1 (1H, m), 5.2–5.4 (1H, m), 7.32 (2H, d), 7.41 (1H, t), 7.79 (2H, d), 7.7–7.9 (1H, m).

On the other hand, 2.5 g of (−)-5-chloro-6-fluoro-2-methyl-4-oxo-1-(N-tosyl-L-prolyl)-1,2,3,4-tetrahydroquinoline was obtained from a fraction having an Rf value of 0.27.

Melting point: 181.5°–182.5° C.

$[\alpha]_D^{20}$: −491.2° (C=1.002, CHCl$_3$).

IR (KBr), cm$^{-1}$: 1685, 1600, 1470 1345.

NMR (CDCl$_3$), δppm: 1.23 (3H, d), 1.6–2.4 (4H, m), 2.39 (3H, s), 2.57 (1H, d), 3.25 (1H, dd), 3.2–3.6 (2H, m), 4.3–4.5 (1H, m), 5.2–5.5 (1H, m), 6.7–7.1 (1H, m), 7.18 (2H, d), 7.2–7.4 (1H, m), 7.32 (2H, d).

(Step b)

25 g of (+)-5-chloro-6-fluoro-2-methyl-4-oxo-1-(N-tosyl-L-prolyl)-1,2,3,4-tetrahydroquinoline obtained in the above step a was suspended in a mixture composed of 680 ml of ethanol and 340 ml of water and containing 14.0 g of sodium hydroxide, and the resulting mixture was stirred at 60° C. for 20 minutes. Then, the ethanol was evaporated under reduced pressure and the resulting concentrate was extracted twice with 200 ml portions of benzene. The extract was washed twice with 100 ml portions of a saturated aqueous solution of sodium chloride, dried and then concentrated under reduced pressure to obtain 10.4 g (90% yield) of (−)-5-chloro-6-fluoro-2-methyl-4-oxo-1,2,3,4-tetrahydroquinoline.

Melting point: 116.8°–119.0° C.

$[\alpha]_D^{20}$: −275.9° (C=0.537, CHCl$_3$)

(Step c)

10.0 g of (−)-5-chloro-6-fluoro-2-methyl-4-oxo-1,2,3,4-tetrahydroquinoline obtained in the above step b was mixed with 16.2 g of diethyl ethoxymethylenemalonate. The resulting mixture was stirred at 170° C. for 3 hours in the absence of solvent and then cooled to about 120° C. This reaction mixture was added dropwise to 80 g of polyphosphoric acid heated to 100°–110° C., over a period of 10 minutes. After completion of the addition, the resulting mixture was stirred at 110°–115° C. for 30 minutes and then cooled to about 90° C. Then, 250 ml of cold water was added thereto and the precipitated crystals were collected by filtration. These crystals were recrystallized from acetic acid to obtain 13.1 g (83% yield) of (−)-8-chloro-9-fluoro-5-methyl-6,7-dihydro-1,7-dioxo-1H,5H-benzo[ij]quinolizine-2-carboxylic acid ethyl ester.

Melting point: 252°–254° C. (foamed and decomposed).

$[\alpha]_D^{20}$: −186.1° (C=0.174, DMF).

IR (KBr), cm$^{-1}$: 1720, 1695, 1660, 1615, 1490, 1430.

Analysis:

Calcd. for C$_{16}$H$_{13}$ClFNO$_4$ (%) C, 56.90; H, 3.88; N, 4.15

Found (%) C, 56.87; H, 3.90; N, 4.18, (Step d)

8.7 g of (−)-8-chloro-9-fluoro-5-methyl-6,7-dihydro-1,7-dioxo-1H,5H-benzo[ij]quinolizine-2-carboxylic acid ethyl ester obtained in the above step c was suspended in 110 ml of chloroform. After the addition of 10.3 g of N-methylpiperazine, the resulting mixture was heated under reflux for 45 minutes. This reaction mixture was washed with water, dried over anhydrous sodium sulfate, and then concentrated under reduced pressure. The residue thus obtained was subjected to silica gel column chromatography using chloroform-ethyl acetate (10:1) as the eluent, and a fraction containing the desired compound was evaporated to dryness. The resulting residue was recrystallized from ethanol to obtain 8.3 g (81% yield) of (+)-9-fluoro-5 methyl-8-(4-methyl-1-piperazinyl)-6,7-dihydro-1,7-dioxo-1H,5H-benzo[ij]quinolizine-2-carboxylic acid ethyl ester.

Melting point: 250°–252° C. (decomposed).
$[\alpha]_D^{20}$: +126.9° (C=0.514, CHCl$_3$).
IR (KBr), cm$^{-1}$: 1730, 1700, 1680, 1620, 1480.
Analysis:
Calcd. for C$_{21}$H$_{24}$FN$_3$O$_4$ (%) C, 62.83; H, 6.03; N, 10.47,
Found (%) C, 62.85; H, 6.11; N, 10.32

(Step e)

7.5 g of (+)-9-fluoro-5-methyl-8-(4-methyl-1-piperazinyl)-6,7-dihydro-1,7-dioxo-1H,5H-benzo[ij]-quinolizine-2-carboxylic acid ethyl ester obtained in the above step d was suspended in 23 ml of ethanol. Then, 3.7 g of sodium hydroxide dissolved in 34 ml of water was added thereto at a temperature of 15° C. or below. The resulting mixture was stirred at 20° C. for 3 hours, adjusted to pH 1 with concentrated hydrochloric acid under cooling with ice, and then allowed to stand in a cold place. The precipitated crystals were collected by filtration and recrystallized from a 40% aqueous solution of ethanol to obtain 6.4 g (80% yield) of (+)-9-fluoro-5-methyl-8-(4-methyl-1-piperazinyl)-6,7-dihydro-1,7-dioxo-1H,5H-benzo[ij]quinolizine-2-carboxylic acid hydrochloride monohydrate.

Melting point: 294°–295° C. (foamed and decomposed).
$[\alpha]_D^{20}$: +139.7° (C=0.559, H$_2$O).
IR (KBr), cm$^{-1}$: 3550, 3450, 1720, 1680, 1630, 1600.
NMR (CF$_3$COOD), δppm: 1 85 (3H, d), 3.25 (3H, s), 3.1–4.4 (10H, m), 5.3–5.5 (1H, m), 8.47 (1H, d), 9.45 (1H, s).
Analysis:
Calcd. for C$_{19}$H$_{20}$FN$_3$O$_4$·HCl·H$_2$O (%) C, 53.34; H, 5.42; N, 9.82
Found (%) C, 53.29; H, 5.53; N, 9.95,

EXAMPLE 2

3.0 g of (+)-9-fluoro-5-methyl-8-(4-methyl-1-piperazinyl)-6,7-dihydro-1,7-dioxo-1H,5H-benzo[ij]-quinolizine-2-carboxylic acid ethyl ester obtained in the step d of Example 1 was suspended in 10 ml of ethanol. Then, 1.5 g of sodium hydroxide dissolved in 14 ml of water was added thereto at a temperature of 15° C. or below. The resulting mixture was stirred at 20° C. for 3 hours, adjusted to pH 4–5 with acetic acid under cooling with ice, and then allowed to stand in a cold place. The precipitated crystals were collected by filtration and recrystallized from water to obtain 2.4 g (83% yield) of (+)-9-fluoro-5-methyl-8-(4-methyl-1-piperazinyl)-6,7-dihydro-1,7-dioxo-1H, 5H-benzo[ij]-quinolizine-2-carboxylic acid monohydrate.

Melting point 228°–229° C. (foamed and decomposed).
$[\alpha]_D^{20}$: +228.4° (C=0.109, 0.02N NaOH).
IR (KBr), cm$^{-1}$: 1735, 1680, 1625, 1600, 1465, 1445.
NMR (CF$_3$COOD), δppm: 1.82 (3H, d), 3.23 (3H, s), 3.3–3.8 (2H, m), 3.8–4.5 (8H, m), 5.1–5.7 (1H, m), 8.37 (1H, d), 9.37 (1H, s).
Analysis:
Calcd. for C$_{19}$H$_{20}$FN$_3$O$_4$·H$_2$O (%) C, 58.31; H, 5.67; N, 10.74
Found (%) C, 58.29; H, 5.63; N, 10.79.

EXAMPLE 3

1.7 g of (−)-8-chloro-9-fluoro-5-methyl-6,7-dihydro-1,7-dioxo-1H,5H-benzo[ij]quinolizine-2-carboxylic acid ethyl ester obtained in the step c of Example 1 was added to 16 ml of acetic acid. After the addition of 4 ml of concentrated hydrochloric acid, the resulting mixture was heated under reflux for 3 hours and then cooled. The precipitated crystals were collected by filtration and recrystallized from acetic acid to obtain 1.26 g (81% yield) of (−)-8-chloro-9-fluoro-5-methyl-6,7-dihydro-1,7-dioxo-1H,5H-benzo[ij]quinolizine-2-carboxylic acid.

Melting point: 294°–296° C. (foamed and decomposed).
$[\alpha]_D^{20}$: −201.7° (C=0.135, 0.02N NaOH).
IR (KBr) cm$^{-1}$: 1745, 1720, 1615, 1470, 1420.
Analysis:
Calcd. for C$_{14}$H$_9$ClFNO$_4$ (%) C, 54.30; H, 2.93; N, 4.52
Found (%) C, 54.23; H, 3.01, N, 4.59, 1.1 g of (−)-8-chloro-9-fluoro-5-methyl-6,7-dihydro-1,7-dioxo-1H,5H-benzo[ij]quinolizine-2-carboxylic acid obtained as above and 1.42 g of N-methylpiperazine were added to 11 ml of methyl cellosolve. The resulting mixture was heated at 80°–100° C. for an hour and then evaporated to dryness. The residue thus obtained were washed with a small amount of methanol These crystals were recrystallized from a 50% aqueous solution of ethanol to obtain 1.04 g (75% yield) of (+)-9-fluoro-5-methyl-8-(4-methyl-1-piperazinyl)-6,7-dihydro-1,7-dioxo-1H, 5H-benzo[ij]quinolizine-2-carboxylic acid monohydrate.

Melting point: 228°–229° C. (foamed and decomposed).
$[\alpha]_D^{20}$: +228.4° (C=0.152, 0.02N NaOH).
IR (KBr), cm$^{-1}$: 1735, 1680, 1625, 1600, 1465, 1445.
NMR (CF$_3$COOD), δppm: 1.82 (3H, d), 3.23 (3H, s), 3.3–3.8 (2H, m), 3.8–4.5 (8H, m), 5.1–5.7 (1H, m), 8.37 (1H, d), 9.37 (1H, s).

EXAMPLE 4

1.5 g of (+)-9-fluoro-5-methyl-8-(4-methyl-1-piperazinyl)-6,7-dihydro-1,7-dioxo-1H,5H-benzo[ij]-quinolizine-2-carboxylic acid ethyl ester obtained in the step d of Example 1 was added to 2 ml of concentrated hydrochloric acid. The resulting mixture was heated under reflux for 6 hours and then concentrated under reduced pressure The residue thus obtained was recrystallized from a 40% aqueous solution of ethanol to obtain 1.38 g (86% yield) of (+)-9-fluoro- 5-methyl-8-(4-methyl-1-piperazinyl)-6,7-dihydro-1,7-dioxo-1H,5H-benzo[ij]quinolizine-2-carboxylic acid hydrochloride monohydrate.

Melting point: 294°–295° C. (foamed and decomposed).
$[\alpha]_D^{20}$: +139.7° (C=0.543, H$_2$0).
NMR (CF$_3$COOD), δppm: 1.85 (3H, d), 3.25 (3H, s), 3.1–4.4 (10H, m), 5.3–5.5 (1H, m), 8.47 (1H, d), 9.45 (1H, s).

EXAMPLE 5

142 g of (+)-3-(2-bromo-5-chloro-4-fluoroanilino)-butyric acid was suspended in 4,000 ml of toluene. Then, 58 g of L-(−)-1-phenylethylamine was added thereto and dissolved therein by the application of heat. The resulting solution was allowed to stand at room temperature for 24 hours and the precipitated crystals were collected in an amount of 43 g. Using 20 parts of toluene, these crystals were recrystallized twice in a similar manner to obtain 10 g of the L-(−)-1-phenylethylamine salt (m.p. 154.5°–155.5° C.) of (+)-3-(2-bromo-5-chloro-4-fluoroanilino)-butyric acid. 9.0 g of this salt was dissolved in 200 ml of chloroform and the resulting solution was shaken with an aqueous solution of phosphoric acid. The chloroform phase was separated and washed twice with 100 ml portions of water. After drying, the chloroform phase was concentrated under reduced pressure to obtain 6.2 g of (+)-3-(2-bromo-5-chloro-4-fluoroanilino)butyric acid in the form of an oil

[60 ]$_D^{20}$: +6.0° C. (C=0.52, CH$_3$OH). IR (KBr), cm$^{-1}$: 3450−2450, 1710, 1600, 1500, 1070. NMR (CDCl$_3$), δppm: 1.35 (3H, d), 2.5–2.8 (2H, m), 3.8–4.0 (1H, m), 6.69 (1H, d), 7.28 (1H, d).

EXAMPLE 6

A mixture composed of 31.1 g of (±)-3-(2-bromo-5-chloro-4-fluoroanilino)butyric acid and 29.4 g of cinchonidine was dissolved in 600 ml of chloroform. Then, the chloroform was evaporated under reduced pressure. The oily residue thus obtained was dissolved in 600 ml of ethyl ether. The resulting solution was allowed to stand at room temperature for 16 hours and the precipitated crystals were collected in an amount of 28.4 g. Using an n-hexane-ethyl acetate mixture (2:1), these crystals were recrystallized four times to obtain 5.8 g of the cinchonidine salt of (+)-3-(2-bromo-5-chloro-4-fluoroanilino)butyric acid. 5.0 g of this salt was dissolved in 100 ml of chloroform and the resulting solution was shaken with an aqueous solution of hydrochloric acid. The chloroform phase was separated and washed twice with water. After drying, the chloroform phase was concentrated under reduced pressure to obtain 2.4 g of (+)-3-(2-bromo-5-chloro-4-fluoroanilino)-butyric acid in the form of an oil. Its specific rotation, IR spectrum and NMR spectrum agreed with those given in Example 5.

EXAMPLE 7

6.0 g of (+)-3-(2-bromo-5-chloro-4fluoroanilino)butyric acid obtained in Example 5 was added to 60 g of a triethyl phosphate-phosphorus pentoxide mixture (in a weight ratio of 3:2). The resulting mixture was stirred at 80°–90° C. for 15 minutes and then cooled to room temperature. After the addition of 600 ml of water, the resulting mixture was stirred and then extracted twice with 150 ml-portions of chloroform. The extract was washed twice with 200 ml-portions of water, dried and then concentrated under reduced pressure. The residue thus obtained was mixed with 0.1 g of 10% palladium-active carbon, 20 ml of a 1N aqueous solution of sodium hydroxide, and 200 ml of methanol. The resulting mixture was stirred at ordinary temperature and pressure for an hour with hydrogen gas passed therethrough. This reaction mixture was filtered to remove the palladium-active carbon therefrom, the filtrate was concentrated under reduced pressure, and the resulting residue was extracted with chloroform. The extract was concentrated under reduced pressure and the resulting residue was purified by silica gel column chromatography [using n-hexane-ethyl acetate (5:1) as the eluent]. Fractions containing the desired compound were collected and concentrated under reduced pressure to obtain 2.2 g of (-)-5-chloro 6-fluoro-2-methyl-4-oxo-1,2,3,4-tetrahydroquinoline.

Its melting point and specific rotation agreed with those given in the step b of Example 1.

EXAMPLE 8

5 mg of (±)-5-chloro-6-fluoro-2-methyl-4-oxo-1,2,3,4-tetrahydroquinoline was dissolved in 5 ml of n-hexane-isopropanol mixture (9:1). 100 μl of this solution was injected into a column. Using this column, high-performance liquid chromatography was carried out under the following conditions.

Column: CHIRALCEL OC (APS) (4.6×250 mm), CHIRALCEL OD (4.6×250 mm) or CHIRALCEL OG (4.6×250 mm). Column temperature: Room temperature. Mobile phase: n-Hexane-isopropanol (9:1). Flow rate: 1.0 ml/min. Detector: Ultraviolet photometer (wavelength 245 nm).

By repeating the above-described procedure, 11 mg each of two optically active (−)- and (+)-isomers were obtained from 24 mg of (±)-5-chloro-6-fluoro-4-oxo-1,2,3,4-tetrahydroquinoline.

[(+)-isomer]

Retention time: 19.0–20.5 minutes for CHIRALCEL OC (APS). 10.0–11.0 minutes for CHIRALCEL OD. 18.5–20.0 minutes for CHIRALCEL OG.

Melting point: 117.0°–119.0° C. [α]$_D^{20}$: +276.0° C. (C=0.103, CHCl$_3$).

[(−)-isomer]

Retention time: 21.5–23.0 minutes for CHIRALCEL OC (APS). 11.5–13.0 minutes for CHIRALCEL OD. 21.0–22.5 minutes for CHIRALCEL OG.

Melting point: 117.8°–119.0° C. [α]$_D^{20}$: −276.0° C. (C=0.101, CHCl$_3$).

EXAMPLE 9

5 mg of (±)-8-chloro-9-fluoro-5-methyl-6,7-dihydro-1,7-dioxo-1H,5H-benzo[ij]quinolizine-2-carboxylic acid ethyl ester was dissolved in 10 ml of methanol. 200 μl of this solution was injected into a column. Using this column, high-performance liquid chromatography was carried out under the following conditions.

Column: CHIRALCEL OC (APS) (4.6×250 mm). Column temperature: Room temperature. Mobile phase: Methanol Flow rate: 1.0 ml/min. Detector: Ultraviolet photometer (wavelength 290 nm), By repeating the above-described procedure, 15 mg each of two optically active isomers were obtained from 34 mg of (+)-8-chloro-9-fluoro-5-methyl-6,7-dihydro-1,7- dioxo-1H,5H-benzo[ij]quinolizine-2-carboxylic acid ethyl ester.

[(+)-isomer]

Retention time: 6.5–7.2 minutes

Melting point: 251°–253° C. (foamed and decomposed). [α$_D^{20}$: +186.9° (C=0.104, DMF). IR (KBr), cm$^{-1}$: 1715, 1695, 1650, 1610, 1485, 1425.

[(−)-isomer]

Retention time: 7.3–8.0 minutes.

Melting point: 252°–254° C. (foamed and decomposed). [α]$_D^{30}$: −186.4° (C=0.102, DMF). IR (KBr), cm$^{-1}$: 1720, 1695, 1660, 1615, 1490, 1430.

EXAMPLE 10

40 mg of (±)-9-fluoro-5-methyl-8-(4-methyl-1-piperazinyl)-6,7-dihydro-1,7-dioxo-1H,5H-benzo[ij]-quinolizine-2-carboxylic acid was dissolved in 4 ml of methanol. After the addition of 0.04 ml of thionyl chloride, the resulting mixture was stirred at 60°–70° C. for an hour. The solvent was evaporated and the resulting residue was dissolved in 4 ml of water. This solution was neutralized with a 0.1N aqueous solution of sodium hydroxide and then extracted with chloroform. The chloroform extract was washed with a saturated aqueous solution of sodium chloride, dried over anhydrous magnesium sulfate, and then freed of solvent. The residue thus obtained was dissolved in 4 ml of methanol and 20 μl of this solution was injected into a column. Using this column, high-performance liquid chromatography was carried out under the following conditions.

Column: CHIRALCEL OC (APS) (4.6×250 mm). Column temperature: Room temperature. Mobile phase: Ethanol (or methanol). Flow rate: 1.0 ml/min. Detector: Ultraviolet photometer (wavelength 290 nm).

By repeating the above-described procedure, 18 mg each of two optically active methyl ester isomers were obtained from 40 mg of (±)-9-fluoro-5-methyl-8-(4-methyl-1-piperazinyl)-6,7-dihydro-1,7-dioxo-1H,5H-benzo[ij]quinolizine-2-carboxylic acid.

[(−)-isomer]

Retention time: 14.0–18.0 minutes (7.0–8.5 minutes for methanol).

Melting point: 255°–256° C. (decomposed). $[\alpha]_D^{20}$: −126.7° (C=0.101, CHCl$_3$). IR (KBr), cm$^{-1}$ 1730, 1700, 1680, 1620, 1470.

Analysis:

Calcd. for $C_{20}H_{22}FN_3O_4$ (%) C, 62.01; H, 5.72; N, 10.85, Found (%) C, 61.94; H, 5.73, N, 10.83.

[(±)-isomer]

Retention time: 19.0–25.0 minutes. (9.0–11.5 minutes for methanol).

Melting point: 255°–256° C. (decomposed). $[\alpha]_D^{20}$: +128.6° (C=0.102, CHCl$_3$). IR (KBr), cm$^{-1}$: 1730, 1700, 1680, 1620, 1470.

Analysis: Calcd. for $C_{20}H_{22}FN_3O_4$ (%) C, 62.01; H, 5.72, N, 10.8, Found (%) C, 61.95; H, 5.71; N, 10.84.

EXAMPLE 11

5 mg of (±)-9-fluoro-5-methyl-8-(4-methyl-1-piperazinyl)-6,7-dihydro-1,7-dioxo-1H,5H-benzo[ij]-quinolizine-2-carboxylic acid was dissolved in 25 ml of methanol. After the addition of a solution of diazomethane in ether, the resulting mixture was stirred at room temperature for 30 minutes. The solvent was evaporated and the resulting residue was dissolved in 0.5 ml of methanol. This solution was treated in the same manner as described in Example 10 to obtain 2.25 mg each of two optically active methyl ester isomers.

EXAMPLE 12

40 mg of (±)-9-fluoro-5-methyl-8-(4-methyl-1-piperazinyl)-6,7-dihydro-1,7-dioxo-1H,5H-benzo[ij]-quinolizine-2-carboxylic acid was dissolved in 4 ml of ethanol. After the addition of 0.04 ml of thionyl chloride, the resulting mixture was stirred at 60°–70° C. for an hour. The solvent was evaporated and the resulting residue was dissolved in 4 ml of water. This solution was neutralized with a 0.1N aqueous solution of sodium hydroxide and then extracted with chloroform. The chloroform extract was washed with a saturated aqueous solution of sodium chloride, dried over anhydrous magnesium sulfate, and then freed of solvent. The residue thus obtained was dissolved in 4 ml of ethanol and 20 μl of this solution was injected into a column. Using this column, high-performance liquid chromatography was carried out under the following conditions.

Column: CHIRALCEL OC (APS) (4.6×250 mm). Column temperature: Room temperature. Mobile phase: Ethanol Flow rate: 1.0 ml/min. Detector: Ultraviolet photometer (wavelength 290 nm).

By repeating the above-described procedure, 18 mg each of two optically active ethyl ester isomers were obtained from 40 mg of (+)-9-fluoro-5-methyl-8-(4-methyl-1-piperazinyl)-6,7-dihydro-1,7-dioxo-1H,5H-benzo[ij]quinolizine-2-carboxylic acid.

[(−)-isomer]

Retention time: 9.0–13.0 minutes.

Melting point: 251°–252° C. (decomposed). $[\alpha]_D^{20}$: −126.0° (C=0.099, CHCl$_3$). IR (KBr), cm$^{-1}$: 1730, 1700, 1680, 1620, 1480.

Analysis: Calcd. for $C_{21}H_{24}FN_3O_4$ (%) C, 62.83; H, 6.03; N, 10.47, Found (%) C, 62.80; H, 6.02; N, 10.46.

(+)-isomer]

Retention time: 14.0–18.0 minutes.

Melting point: 251°–252° C. (decomposed). $[\alpha]_D^{20}$+126.1° (C=0.103, CHCl$_3$). IR (KBr), cm$^{-1}$: 1730, 1700, 1680, 1620, 1480.

Analysis: Calcd. for $C_{21}H_{24}FN_3O_4$ (%) C, 62.83; H, 6.03; N, 10.47, Found (%) C, 62.81; H, 6.01; N, 10.48.

EXAMPLE 13

60 mg of (+)-9-fluoro-5-methyl-8-(4-methyl-1-piperazinyl)-6,7-dihydro-1,7-dioxo-1H,5H-benzo[ij]-quinolizine-2-carboxylic acid hydrochloride monohydrate was dissolved in 12 ml of water. 50 μl of this solution was injected into a column. Using this column, high-performance liquid chromatography was carried out under the following conditions.

Column: YMC-Pack A-302 (4.6×250 mm). Column temperature: Room temperature. Mobile phase: A solution obtained by mixing a 6 mM aqueous copper sulfate solution, a 6 mM amino acid solution and methanol in a volume ratio of 17:17:6 and then adjusting the resulting mixture to pH 5.0 with a 1N aqueous solution of sodium acetate. Flow rate: 1.0 ml/min. Detector: Ultraviolet photometer (wavelength 290 nm)

Using each of several amino acids, two optically active copper complexes, a (+)-isomer-amino acid-copper complex and a (−)-isomer-amino acid-copper complex were obtained from (±)-9-fluoro-5-methyl-8-(4-methyl-1-piperazinyl)-6,7-dihydro-1,7-dioxo-1H,5H-benzo[ij]quinolizine-2-carboxylic acid hydrochloride monohydrate.

The amino acids used, the retention times (A) of the obtained (+)-isomer-amino acid-copper complexes, and the retention times (B) of the obtained (-)-isomer-amino acid-copper complexes are given below.

| Amino acid | A (minutes) | B (minutes) |
|---|---|---|
| L-valine | 9.0–11.0 | 11.0–13.0 |
| L-leucine | 17.0–20.0 | 21.0–24.0 |
| L-isoleucine | 17.0–20.0 | 21.0–24.0 |
| L-phenylalanine | 19.5–22.0 | 22.0–25.0 |
| D-phenylalanine | 23.0–26.0 | 20.0–23.0 |

By repeating the above-described procedure, two optically active copper complexes, a (+)-isomer-amino acid-copper complex and a (−)-isomer-amino acid-copper complex were obtained from 60 mg of (±)-9-fluoro-5-methyl-8-(4-methyl-1-piperazinyl)-6,7-dihydro-1,7-dioxo-1H,5H-benzo[ij]quinolizine-2-carboxylic acid hydrochloride monohydrate.

Each of the fractions containing the (+)-isomer-amino acid-copper complex and the (−)-isomer-amino acid-copper complex was concentrated under reduced pressure and the resulting residue was dissolved in water. This solution was treated with Amberlite IRC-718 in the vicinity of pH 2, adjusted to pH 7.0 with a 0.1N aqueous solution of sodium hydroxide, and then extracted with chloroform. The chloroform extract was washed with a saturated aqueous-solution of sodium chloride, dried over anhydrous magnesium sulfate, and then concentrated under reduced pressure. The resulting residue was dissolved in 0.4 ml of water and this solution was adjusted to pH 1 with concentrated hydrochloric acid under cooling with ice. After the addition of 0.3 ml of ethanol, the resulting mixture was allowed to stand in a cold place. The precipitated crystals were collected by filtration and recrystallized from a 40% aqueous solution of ethanol. Thus, there were obtained 25 mg of (+)-9-fluoro-5-methyl-8-(4-methyl-1-piperazinyl)-6,7-dihydro-1,7-dioxo-1H,5H-benzo[ij]-quinolizine-2-carboxylic acid hydrochloride monohydrate and 25 mg of (−)-9-fluoro-5-methyl-8-(4-methyl-1-piperazinyl)-6,7-dihydro-1,7 dioxo-1H,5H-benzo[ij]-quinolizine-2-carboxylic acid hydrochloride monohydrate.

[(+)-isomer]

Melting point: 294°–295° C. (foamed and decomposed). $[\alpha]_D^{20}$: +140.0° (C=0.102, H$_2$O ). IR (KBr), cm$^{-1}$: 3550, 3450, 1720, 1680, 1620, 1600. NMR (CF$_3$COOD), δppm: 1.85 (3H, d), 3.25 (3H, s), 3.1–4.4 (10H, m), 5.3–5.5 (1H, m), 8.47 (1H, d), 9.45 (1H, s).

Analysis: Calcd. for C$_{19}$H$_{20}$FN$_3$O$_4$·HCl·H$_2$O (%) C, 53.34; H, 5.42; N, 9.82, Found (%) C, 53.30; H, 5.43; N, 9.84.

[(−)-isomer]

Melting point: 294°–295° C. (foamed and decomposed). $[\alpha]_D^{20}$: −138.1° (C=0.102, H$_2$O ). IR (KBr), cm$^{-1}$: 3520, 3450, 1720, 1680, 1625, 1600. NMR (CF$_3$COOD), δppm: 1.85 (3H, d), 3.26 (3H, s), 3.1–4.5 (10H, m), 5.3–5.5 (1H, m), 8.47 (1H, d), 9.45 (1H, s).

Analysis:
Calcd. for C$_{19}$H$_{20}$FN$_3$O$_4$·HCl·H$_2$O (%) C, 53.34; H, 5.42; N, 9.82, Found (%) C, 53.36; H, 5.44; N, 9.80.

Now, the preparation of a compound [I]-(−) is illustrated by the following reference example.

REFERENCE EXAMPLE

Using 2.2 g of (−)-5-chloro-6-fluoro-2-methyl-4-oxo-1-(N tosyl-L-prolyl)-1,2,3,4-tetrahydroquinoline which had been obtained in the step a of Example 1 from the fraction having an Rf value of 0.27, the procedure described in the step b of Example 1 was followed. Thus, there was obtained 0.90 g (89% yield) of (+)-5-chloro-6-fluoro-2-methyl-4-oxo-1,2,3,4-tetrahydroquinoline.

Melting point: 116.8°–119.0° C., $[\alpha]_D^{20}$: +276.1° (C=0.521, CHCl$_3$).

Using 0.70 g of (+)-5-chloro-6-fluoro-2-methyl-4-oxo-1,2,3,4-tetrahydroquinoline obtained as above, the procedure described in the step c of Example 1 was followed. Thus, there was obtained 0.94 g (85% yield) of (+)-8-chloro-9-fluoro-5-methyl-6,7-dihydro-1,7-dioxo1H,5H-benzo[ij]quinolizine-2-carboxylic acid ethyl ester.

Melting point: 251°–253° C. (foamed and decomposed). $[\alpha]_D^{20}$: +187.2° (C=0.176, DMF). IR (KBr), cm$^{-1}$: 1715, 1695, 1650, 1610, 1485, 1425.

Using 0.80 g of (+)-8-chloro-9-fluoro-5-methyl-6,7-dihydro-1,7-dioxo-1H,5H-benzo[ij]quinolizine-2-carboxylic acid ethyl ester obtained as above and 0.95 g of N-methylpiperazine, the procedure described in the step d of Example 1 was followed. Thus, there was obtained 0.78 g (82% yield) of (−)-9-fluoro-5-methyl-8-(4-methyl-1-piperazinyl)-6,7-dihydro-1,7-dioxo-1H,5H-benzo[ij]quinolizine-2-carboxylic acid ethyl ester.

Melting point: 249°–251° C. (decomposed). $[\alpha]_D^{20}$: −126.5° (C=0.521, CHCl$_3$). IR (KBr), cm$^{-1}$: 1730, 1700, 1680, 1620, 1480.

Using 0.60 g of (−)-9-fluoro-5-methyl-8-(4-methyl-1-piperazinyl)-6,7-dihydro-1,7-dioxo-1H,5H-benzo[ij]-quinolizine-2-carboxylic acid ethyl ester obtained as above, the procedure described in the step e of Example 1 was followed. Thus, there was obtained 0.50 g (78% yield) of (−)-9-fluoro-5-methyl-8-(4-methyl-1-piperazinyl)-6,7-dihydro-1,7-dioxo-1H,5H-benzo[ij]-quinolizine-2-carboxylic acid hydrochloride monohydrate.

Melting point: 294°–295° C. (foamed and decomposed). $[\alpha]_D^{29}$: −138.2° (C=0.499, H$_2$O ). IR (KBr), cm$^{-1}$: 3520, 3450, 1720, 1680, 1625, 1600. NMR (CF$_3$COOD), δppm: 1.85, (3H, d), 3.26 (3H, s), 3.1–4.5 (10H, m), 5.3–5.5 (1H, m), 8.47 (1H, d), 9.45 (1H, s).

Analysis: Calcd. for C$_{19}$H$_{20}$FN$_3$O$_4$·HCl·H$_2$O (%) C, 53.34; H, 5.42; N, 9.82, Found (%) C, 53.32; H, 5.49; N, 9.76.

We claim:

1. An optically active (+)-isomer of a benzoquinolizine compound of the formula

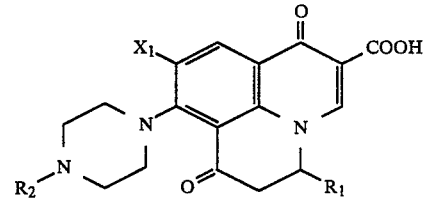

where X$_1$ represents a halogen atom, and R$_1$ and R$_2$ represent lower alkyl groups, a physiologically acceptable salt thereof, or a hydrate of either of the foregoing compounds.

2. The compound of claim 1 which is (+)-9-fluoro-5-methyl-8-(4-methyl-1-piperazinyl)-6,7-dihydro-1,7-dioxo-1H,5H-benzo[ij]quinolizine-2-carboxylic acid, a physiologically acceptable salt thereof, or a hydrate of either of the foregoing compounds.

3. An optically active (+)-isomer of a benzoquinolizine compound of the formula

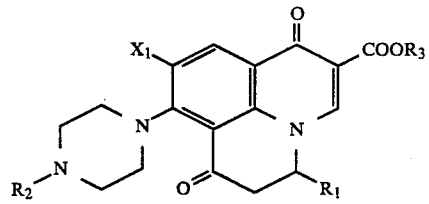

where X$_1$ represents a halogen atom, and R$_1$, R$_2$ and R$_3$ represent lower alkyl groups.

4. The compound of claim 3 which is (+)-9-fluoro-5-methyl-8-(4-methyl-1-piperazinyl)-6,7-dihydro-1,7-dioxo-1H,5H-benzo[ij]quinolizine-2-carboxylic acid methyl ester or (+)-9-fluoro-5-methyl-8-(4-methyl-1-piperazinyl)-6,7-dihydro-1,7-dioxo-1H,5H-benzo[ij]-quinolizine-2-carboxylic acid ethyl ester.

5. An optically active (−)-isomer of a benzoquinolizine compound of the formula

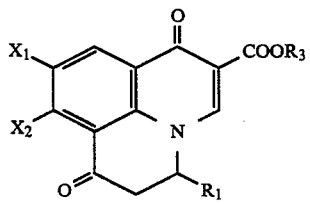

where $X_1$ and $X_2$ represent halogen atoms, and $R_1$ and $R_3$ represent lower alkyl groups.

6. The compound of claim 5 which is (−)-8-chloro-9-fluoro-5-methyl-6,7-dihydro-1,7-dioxo-1H,5H-benzo[ij]quinolizine-2 carboxylic acid ethyl ester.

7. An optically active (−)-isomer of a quinoline compound of the formula

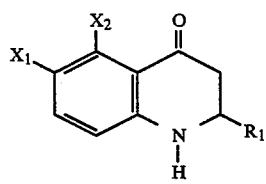

where $X_1$ and $X_2$ represent halogen atoms, and $R_1$ represents a lower alkyl group.

8. The compound of claim 7 which is (−)-5-chloro-6-fluoro-2-methyl-4-oxo-1,2,3,4-tetrahydroquinoline.

9. An optically active (+)-isomer of an anilinobutyric acid compound of the formula

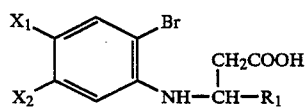

where $X_1$ and $X_2$ independently represent fluorine or chlorine atoms, and $R_1$ represents a lower alkyl group.

10. The compound of claim 9 which is (+)-3-(2-bromo-5-chloro-4-fluoroanilino)butyric acid.

11. A process for preparing an optically active (+)-isomer of a benzoquinolizine compound of the formula

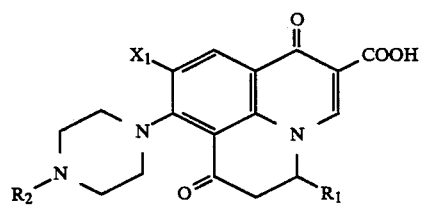

where $X_1$ represents a halogen atom, and $R_1$ and $R_2$ represent lower alkyl groups, a physiologically active salt thereof, or a hydrate of either of the foregoing compounds, which comprises optically resolving the benzoquinolizine compound in a solvent containing a metallic ion and an amino acid, with the aid of a resolving agent containing octadecylsilylated silica gel as a component.

12. A process for preparing an optically active (+)-isomer of a benzoquinolizine compound of the formula

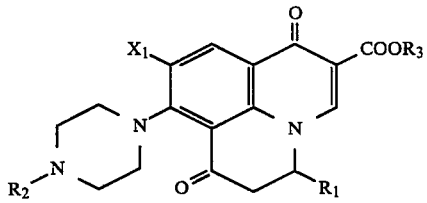

where $X_1$ represents a halogen atom, and $R_1$, $R_2$ and $R_3$ represent lower alkyl groups, which comprises optically resolving the benzoquinolizine compound with the aid of a resolving agent containing a polysaccharide compound as an active component.

13. A process for preparing an optically active (−)-isomer of a benzoquinolizine compound of the formula

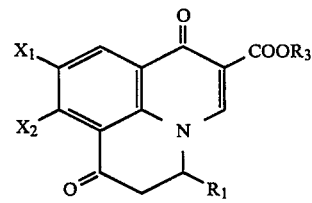

where $X_1$ and $X_2$ represent halogen atoms, and $R_1$ and $R_3$ represent lower alkyl groups, which comprises optically resolving the benzoquinolizine compound with the aid of a resolving agent containing a polysaccharide compound as an active component.

14. A process for preparing an optically active (−)-isomer of a quinoline compound of the formula

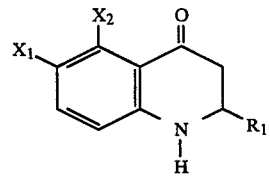

where $X_1$ and $X_2$ represent halogen atoms, and $R_1$ represents a lower alkyl group, which comprises optically resolving the quinoline compound with the aid of a resolving agent containing a polysaccharide compound as an active component.

15. A process for preparing an optically active (+)-isomer of an anilinobutyric acid compound of the formula

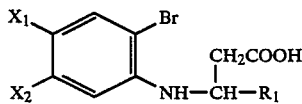

where $X_1$ and $X_2$ independently represent fluorine or chlorine atoms, and $R_1$ represents a lower alkyl group, which comprises optically resolving the anilinobutyric acid compound with the aid of a resolving agent comprising an optically active amine.

16. A process for preparing an optically active (+)-isomer of a benzoquinolizine compound of the formula

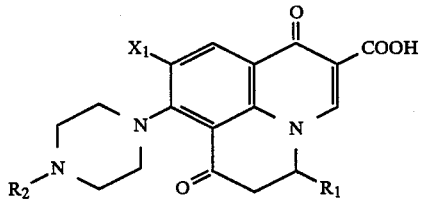

where $X_1$ represents a halogen atom, and $R_1$ and $R_2$ represent lower alkyl groups, a salt thereof, or a hydrate of either of the foregoing compounds, which comprises hydrolyzing a (+)-isomer of a benzoquinolizine compound of the formula

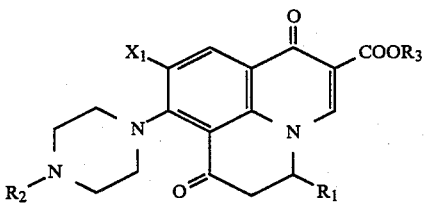

where $X_1$ represents a halogen atom, and $R_1$, $R_2$ and $R_3$ represent lower alkyl groups.

17. A process for preparing an optically active (+)-isomer of a benzoquinolizine compound of the formula

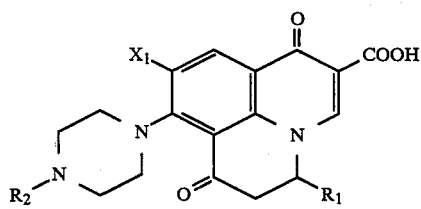

where $X_1$ represents a halogen atom, and $R_1$ and $R_2$ represent lower alkyl groups, a physiologically acceptable salt thereof, or a hydrate of either of the foregoing compounds, which comprises effecting nucleophilic substitution reaction between an optically active (−)-isomer of a benzoquinolizine compound of the formula

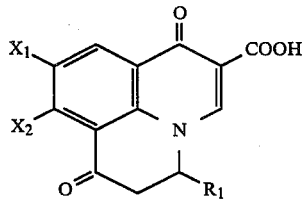

where $X_1$ and $X_2$ represent halogen atoms, and $R_1$ represents a lower alkyl group, and a piperazine compound of the formula

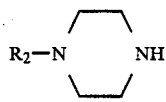

where $R_2$ represents a lower alkyl group.

18. An antibacterial composition comprising a pharmaceutical carrier or diluent and an antibacterially effective amount of an optically active (+)-isomer of a benzoquinolizine compound of the formula

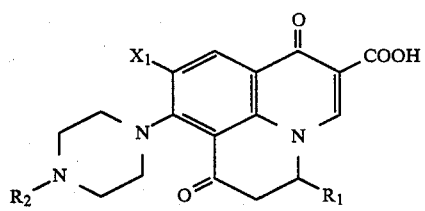

where $X_1$ represents a halogen atom, and $R_1$ and $R_2$ represent lower alkyl groups, a physiologically acceptable salt thereof, or a hydrate of either of the foregoing compounds.

19. The antibacterial preparation of claim 18 wherein the active ingredient comprises (+)-9-fluoro-5-methyl-8-(4-methyl-1-piperazinyl)-6,7-dihydro-1,7-dioxo-1H,5H-benzo[ij]quinolizine-2-carboxylic acid, a physiologically acceptable salt thereof, or a hydrate of either of the foregoing compounds.

20. A method of treating infectious disease comprising administering a compound of claim 1.

21. A method as claimed in claim 20 wherein said compound is (+)-9-fluoro-5-methyl-8-(4-methyl-1-piperazinyl)-6,7-dihydro-1,7-dioxo-1H,5H-benzo[ij]-quinolizine-2-carboxylic acid, a physiologically acceptable salt thereof, or a hydrate of either of the foregoing compounds.

* * * * *